United States Patent [19]

Weetall

[11] 4,188,371

[45] Feb. 12, 1980

[54] IMMUNOLOGICAL DETECTION OF NEISSERIA BACTERIA VIA LABELLED ANTIBODIES

[75] Inventor: Howard H. Weetall, Big Flats, N.Y.

[73] Assignee: Corning Glass Works, Corning, N.Y.

[21] Appl. No.: 837,362

[22] Filed: Sep. 28, 1977

[51] Int. Cl.² .................... G01N 33/16; A61K 43/00
[52] U.S. Cl. ..................... 424/1; 23/230 B; 424/8; 424/12
[58] Field of Search ............ 424/1, 1.5, 8, 12; 23/230 B

[56] References Cited

U.S. PATENT DOCUMENTS

| | | | |
|---|---|---|---|
| 3,974,269 | 8/1976 | Maley | 424/1.5 |
| 4,029,756 | 6/1977 | Gaafar | 424/1 |
| 4,066,744 | 1/1978 | Price et al. | 23/230 B |

OTHER PUBLICATIONS

Tramont et al., Journal of Infectious Diseases, vol. 130, No. 3, Sep. 1974, pp. 240–247.

Primary Examiner—Benjamin R. Padgett
Assistant Examiner—Christine M. Nucker
Attorney, Agent, or Firm—William E. Maycock; Clinton S. Janes, Jr.

[57] ABSTRACT

This invention is concerned with two closely related assay methods for detecting the presence of Neisseria bacteria in a fluid sample. Both of the methods utilize radiolabelled antibodies specific to the enzyme released upon lysis of the bacteria. In the first method, denominated immunoradiometric assay (IRMA), the enzyme is reacted with soluble purified radioactive antibodies. In the second method, known variously as "two-site IRMA", "junction test", or "sandwich technique", contemplates initial insolubilization of the enzyme and thereafter the reaction with soluble purified radioactive antibodies.

The structure and composition of the enzyme released upon lysis of Neisseria bacteria are not fully comprehended but it has the capability of oxidizing 1,2-propanediol and reducing nicotinamide-adenine-dinucleotide (NAD). This has led to the name 1,2-propanediol dehydrogenase being proposed for the enzyme.

20 Claims, No Drawings

IMMUNOLOGICAL DETECTION OF NEISSERIA BACTERIA VIA LABELLED ANTIBODIES

RELATED APPLICATIONS

Patent Application Ser. No. 837,366, filed of even date by the present applicant entitled "Detecting Neisseria Bacteria", Patent Application Ser. No. 837,365, filed of even date by the present applicant entitled "Comparative Test for Neisseria", Patent Application Ser. No. 837,364 filed of even date by the present applicant entitled "Detection of Neisseria Bacteria by Immunoassay", Patent Application Ser. No. 837,363, filed of even date by the present applicant entitled "Immunoassay of Neisseria Bacteria Via $(NH_4)_2SO_4$ Precipitation", Patent Application Ser. No. 837,360, filed of even date by H. C. McDonald entitled "Detection and Quantitation of Neisseria Via Radioimmunoassay of an Enzyme Present in Neisseria Bacteria", and Patent Application Ser. No. 837,361, filed of even date by M. M. Takeguchi and the present applicant entitled "Transport System for Clinical Systems", each of said applications being assigned to the assignee of the instant application.

BACKGROUND OF THE INVENTION

This disclosure is concerned generally with processes for detecting the presence of Neisseria bacteria utilizing labelled antibodies.

The importance of being able to quickly and accurately determine the presence of Neisseria bacteria, particularly *Neisseria gonorrhoeae*, is well-appreciated. Conventional tests for detecting the presence of organisms such as *N. gonorrhoeae* require the preparation of bacteria cultures or the use of serological methods. Such tests, however, have well-recognized limitations. See, for example, the publication "International Symposium on Gonorrhea", B. B. Diena, Ed., a collection of papers presented at the October, 1973 International Symposium on Gonorrhea sponsored by the Health Protection Branch, Health and Welfare Canada, Ottawa, especially at page 34 et seq.

A relatively simple and quick enzymatic test for the presence of Neisseria bacteria is disclosed in the related patent application cited above entitled "Detecting Neisseria Bacteria". That test is based upon the discovery of an enzyme in Neisseria bacteria which is released during lysis thereof which appears to be specific to Neisseria bacteria. Although the full structure and composition of the enzyme has not been explained and no identification therefor has been found in the literature, the enzyme has the capability for oxidizing 1,2-propanediol and reducing nicotinamide-adenine-dinucleotide (NAD) to NADH. In view of those property characteristics, the name 1,2-propanediol dehydrogenase has been suggested for the enzyme, and that appellation will be used throughout this specification.

In another related application cited above entitled "Detection of Neisseria Bacteria by Immunoassay" is disclosed the use of antibodies to inhibit the activity of the enzyme 1,2-propanediol dehydrogenase. And in yet another application cited above entitled "Immunoassay of Neisseria Bacteria Via $(NH_4)_2SO_4$ Precipitation" is disclosed a modification of that method wherein $(NH_4)_2SO_4$ precipitation of the antigen-antibody complex acts to concentrate the enzyme, remove interfering materials, and thereby improve the speed and precision of the assay.

Immunological reactions are recognized as being highly specific biochemical reactions wherein a first protein, known as the antigen, bonds with a protein specific to the antigen, termed on antibody, to form an immunologically complexed protein. In the vast majority of instances, the reaction will occur even when the antigen is modified through the addition of a radioactive label or tracer. The antibody-antigen complexes formed thereby are radioactive and can be separated from uncomplexed reactants by various well-established means. Inasmuch as the measurement of radioactivity is a known and sensitive procedure, a quantitative assay is possible for any protein to which a specific antibody is available.

Two closely related assay methods utilizing radiolabelled antibodies to convert an unknown soluble antigen into a radioactive product are discussed in "Handbook of Radioimmunoassay", edited by Guy E. Abraham, Vol. 5, Chap. 4, pages 131–177, Marcel Dekker, Inc., New York and Basel (1977).

The first method, termed immunoradiometric assay (IRMA), contemplates the following general procedure. The unknown antigen is first reacted with soluble purified radiolabelled antibodies. The radiolabelled complex remains in solution while unused radiolabelled antibodies are removed via a second reaction with a solid phase antigen or antigen immunoadsorbent. The amount of radioactivity remaining in solution is a direct function of the antigen concentration.

The second method, variously termed "two-site IRMA", "junction test", and "sandwich technique", contemplates first the insolubilization of the unknown antigen by reaction with solid phase antibodies, and then carrying out the reaction with soluble labelled antibody. In this practice, the labelled complex is insoluble and unreacted labelled antibody can be washed away. An increase in the amount of unknown antigen results in an increase in radioactivity in the solid phase. The use of this second method is limited to antigens which can either (1) bind simultaneously to at least two antibodies, or (2) bind to a radiolabelled antibody after some nonimmunological insolubilization procedure.

Thus, any particular proteinaceous material will consist of various entities, e.g., protein molecules, cells, etc., which do not adhere to each other. Accordingly, proteinaceous matter deposits as a single layer when brought into contact with a substrate. And no other arbitrary protein will adhere to the layer of deposited protein. Nevertheless, a protein which will specifically react to the protein adsorbed onto or chemically bonded, e.g., covalently bonded, to the substrate will immunologically bond thereto. This phenomenon has given rise to immunoassay methods utilizing the "sandwich technique" whereby a layered structure is formed on a base substrate.

Those methods can be generally described as comprising the following steps. A substrate is prepared having a first layer of a protein physically adsorbed or covalently bonded thereon which can be utilized to test suspected solutions for the presence of a protein specifically reactive to the adsorbed or covalently bonded protein. The substrate having the adsorbed protein is then contacted with a medium containing the substance to be analyzed, this substance including particles which bond to the proteinaceous matter adsorbed on the substrate. Finally, the two-layer composite is contacted with a medium containing labelled or tagged antibodies to the particles of the second layer. Customarily, the label or tag will consists of a radioactive isotope or a fluorescent group from which emanations occur. Such a unit can be chemically integrated into an entity which, because of its presence in extremely dilute concentrations, is itself exceedingly difficult to detect, and which, because of the emanations arising therefrom, can be readily detected even in very small quantities. Therefore, detection of the labelling or tagging unit simultaneously confirms the presence of the entity into which it is integrated.

In summary, a composite or sandwich is produced comprising a first or inner layer containing unlabelled antibodies immobilized on a substrate; a second or intermediate layer containing antigens which are bonded to the immobilized antibodies; and a third or outer layer having labelled antibodies which are bonded to the antigens of the intermediate layer. The surface of the composite is monitored for the presence of the labelling or tagging units.

The general steps contemplated in IRMA are set out below wherein Ag refers to antigen and Ab* designates purified radiolabelled antibodies:

(1) Ag+Ab*→AgAb*+Ab*

(2)
AgAb* + Ab* + solid phase Ag → AgAb* +
(supernatant)

(residue to discard)
solid phase AgAb*

The general steps involved in two-site IRMA or the sandwich technique are reported below wherein Ab refers to antibody, Ag designates antigen, and Ab* describes purified radiolabelled antibodies:

(3) solid phase Ab+Ag→insolubilized Ag (4) insolubilized Ag+Ab*→insolubilized AgAb*+Ab*

(5) insolubilized AgAb*+Ab* $\xrightarrow{wash}$ remove Ab*

It will be appreciated that these two methods differ from conventional radioimmunoassay (RIA) in that the antigen to be measured is assayed directly by reaction with excess radiolabelled antibodies, rather than by competition with a labelled antigen derivative for a limited amount of antibody. The related case cited above entitled "Detection and Quantitation of Neisseria by the Radioimmunoassay of an Enzyme Present in Neisseria Bacteria" is illustrative of a typical radioimmunoassay method. Thus, the IRMA and RIA techniques are compared below:

```
       IRMA                    RIA
Ag + Ab* ⇌ AgAb*   Ag* + Ab + Ag ⇌ Ag*Ab + AgAb
  (Ab* excess)              (limiting Ab)
```

The asterisk denotes radiolabelling.

In general, the sandwich technique provides better sensitivity, i.e., the minimal detectable quantity is lower, than IRMA. Likewise, the precision and accuracy of the sandwich technique are generally superior to those of IRMA. Consequently, those advantages have led to the former method of assay to be preferred and the working examples provided hereinbelow are directed to the two-site IRMA or sandwich technique.

SUMMARY OF THE INVENTION

The IRMA method of the invention contemplates the following general steps:

(1) bringing radiolabelled antiserum specific to 1,2-propanediol dehydrogenase into contact with a lysate of the sample to be tested and incubating the mixture;

(2) bringing a solid phase antigen or antigen immunoadsorbent into contact therewith and incubating the mixtures; and then (3) monitoring the radioactivity of the supernatant.

The solid phase antigen can consist of a glass, ceramic, plastic, or other substrate to which 1,2-propanediol dehydrogenase is immobilized, either through physical adsorption or via such chemical coupling as covalent bonding. An immunoadsorbent matrix such as m-aminobenzyloxymethyl cellulose (ABMC) may also be utilized. The 1,2-propanediol dehydrogenase will be chemically coupled thereto. The substrate material and the immunoadsorbent matrix must be inert to the reactants, including the radioactive label.

The two-site IRMA or sandwich technique method of the invention involves the following general steps:

(1) preparing an antiserum specific to 1,2-propanediol dehydrogenase;

(2) immobilizing said antiserum on a substrate via physical adsorption or covalent bonding;

(3) preparing a lysate of the sample to be tested;

(4) applying said lysate onto said immobilized antiserum on the substrate and incubate;

(5) preparing an antiserum specific to 1,2-propanediol dehydrogenase which is radioactive or other means labelled;

(6) applying said labelled antiserum onto said lysate and incubate; and then (7) monitoring the surface of the resulting composite body made up of said labelled antiserum for the presence of said labelling units.

In the preferred embodiment the antiserum will be radioactively labelled, e.g., with $I^{125}$, and the monitoring accomplished by means of coventional gamma ray counter utilizing a scintillator crystal. However, the basis inventive technique is also operable with fluorescent labelled antisera.

SPECIFIC EMBODIMENTS

A method for preparing an operable lysate is disclosed in the above-cited related application entitled "Detecting Neisseria Bacteria" and that method can also be employed here. The objective of the lysing practice is to release intracellular content, including enzymes, from a sample, e.g., human body fluid or exudate. The lysing procedure need only be conducted in such a manner and under such conditions that denaturing of the enzyme of interest is avoided.

In the following exemplary embodiments, a suspension of *N. gonorrhoea* bacteria was prepared in 0.3M TRIS buffer, pH 9.0. The suspension was compounded in a manner to contain about $10^5$ bacteria, as determined via an absorbency of 0.1 on a Spec 20 spectrophotometer. To 50 ml of the suspension at 0° C. were added 5 ml of a 0.1% solution of egg-white lysozyme (Biozyme Laboratories) prepared in 0.03M TRIS buffer, pH 9.0. This bacteria-buffer-lysozyme mixture was mixed together and allowed to stand briefly. Then 5 ml of a 0.1% solution of EDTA (ethylene diamine tetraacetic acid) in 0.03M TRIS buffer pH 9.0 were added and the resulting mixture agitated in a shaker bath for 10 minutes at 12 reciprocating cycles/five seconds. The EDTA acts as a chelating agent to bond with any divalent metal ions present which might interfere with the activity of the enzyme. Other chelating agents may be used so long as the bacteria-buffer-lysozyme reaction is not deleteriously affected. Thus, the inclusion of EDTA is not mandatory but comprises a useful precaution. Lysis was permitted to continue for one hour at 0° C. Thereafter, the mixture was centrifuged for 10 minutes at 5000 rpm and the supernatant decanted off, this supernatant constituting the lysate.

The 1,2-propanediol dehydrogenase enzyme contained within the supernatent was purified utilizing an affinity column as described, e.g., by Lee, Chi-Yu, D. A. Loppi, B. Wermuth, J. Everse, and N.O. Kaplan, *Arch. Biochem. Biophys.* 163, 561–569, 1974. Thus, to a column containing approximately 60 ml agarose-AMP (adenosine monophosphate) are added 30 ml of the supernatant diluted in half with 0.02M $KH_2PO_4$, pH 6.0. The supernatant is washed through and followed with more buffer until the optical density at 280 nm is near zero when viewed with a Perkin-Elmer double beam spectrometer. The enzyme is eluted with 0.5 mM NADH (40 mg/100 ml) in 0.02M $KH_2PO_4$, pH 6.0. The active fractions are combined and lyophilized either before or after dialysis. Sodium dodecylphosphate gels or agarose gel indicate that the enzyme is at least 95% pure.

An antiserum is prepared in the known manner which can be used as such or in the form of a globulin fraction of the antibody. The antibody was titered by utilizing the specificity of the antibody to the enzyme to block enzyme activity during the complexing reaction. This was accomplished in the following manner:

(1) to 0.1 ml of antiserum dilution was added 0.1 ml of the *N. gonorrhoeae* lysate containing 5–10 units of activity (one unit causes an optical density change at 280 nm of 0.01/min.);

(2) the mixture is incubated for one hour at 0° C.;

(3) to 0.1 ml of the mixture were admixed 2.75 ml 0.1M TRIS, pH 9.0, 0.1 ml (10 mg/ml) NAD, and 0.05 ml 1,2-propanediol. The assay was monitored by increasing absorbence at 340 nm employing the above-mentioned double beam spectrometer. The table below reports the results.

| Antiserum Dilution | Units/Minute | % Inhibition |
|---|---|---|
| Undiluted | 0.2 | 96 |
| 1:2 | 0.2 | 96 |
| 1:4 | 0.5 | 90 |
| 1:8 | 0.8 | 84 |
| 1:16 | 1.5 | 70 |
| 1:32 | 3.8 | 24 |
| 1:64 | 4.3 | 14 |
| No antiserum | 5.0 | 0 |

It is apparent from the table that, as the antiserum is diluted, less inhibition of the enzyme activity occurs. Not only does this factor permit titering of the antiserum but also it proves the specificity of the antiserum for the 1,2-propanediol dehydrogenase isolated from the *N. gonorrhoeae*.

The antiserum can be labelled with an isotope of iodine, e.g., $I^{125}$, following the general chloramine T procedure described by Greenwood, F.C., Hunter, W.M., and Glover, J.S., in "The Preparation of I-131 Labeled Human Growth Hormone of High Specific Radioactivity", *Biochem.* 89, 114–123, 1963. For use in the succeeding exemplary embodiments, the following procedure was employed.

To a small glass reaction vessel held within an ice bath were added 1 mg antiserum in 0.025–0.05 ml 0.03M phosphate buffered saline solution (PBS), pH 7.5, 0.5 mci $I^{125}$ NaOH in 0.05 ml 0.5M PBS, pH 7.5, and 0.1 ml chloramine T solution. The solution was agitated while in the ice bath for about 30 seconds to allow a reaction between the three components to take place. The reaction is then quenched via the addition of 0.2 ml sodium metabisulfite solution (24 mg/10 ml) in 0.03M PBS, pH 7.5. 0.2 ml KI solution (10 mg/ml) in 0.03M PBS, pH 7.5, is admixed to the reaction product.

Thereafter, a column was prepared employing a 10 ml glass pipette packed with G-50 Sephadex swollen in distilled $H_2O$. (G-50 Sephadex is a gel fitration medium marketed by Phamacia Fine Chemicals, Inc., Piscataway, N.J.) The column was washed with 10-20 ml 0.03M PBS, pH 7.5, and then 5 ml of a 2% gelatin solution introduced to coat the column. The column was again washed with 10-20 ml 0.03M PBS, pH 7.5, with the buffer head level being taken down to the column bed.

The $I^{125}$-containing reaction mixture was then allowed to flow into the column and 0.5 ml fractions were collected. Thereafter, 1 ml 0.03M PBS was placed on top of the column and the buffer permitted to lower to the column bed. Elutrication was begun with 0.3M PBS, pH 7.5, by establishing a buffer head of about 5 ml and about 30–40 cuts were collected. Labelled protein was removed from the column at about 10–11 cuts. The iodide front was monitored as it was eluted off the column by means of a portable ratemeter (small Geiger Counter).

A glass support or substrate was employed and the antisera normally immobilized thereon through covalent bonding utilizing the conventional azo-linkage or N-hydroxysuccinic ester methods. Such methods provide stronger bonds than simple adsorption. No substantive differences in effectiveness could be observed between the two coupling techniques so they were used interchangeably. Likewise, the use of porous or non-porous glass as the support material appeared to have no essential effect upon the final result. Other types of substrates are operable, e.g., glass, metals, plastics, or ceramics, so long as no adverse reaction takes place between the substrate material and the antiserum.

EXAMPLE 1

Porous glass beads of a borosilicate composition were utilized as the substrate and 250 mg antiserum diluted to 10 ml in 0.01M borate buffered saline (BBS) with 0.1% bovine serum albumin (BSA) and 0.2% Triton-X-100 (a detergent marketed by Rohm and Haas, Philadelphia, Pennsylvania), pH 7.5, were immobilized on the surfaces thereof using the conventional azo-linkage coupling technique.

To 0.1 ml of *N. gonorrhoeae* lysate were mixed 0.1 ml of the above immobilized antiserum (about 2.5 mg), 0.8 ml of the above buffer solution, and 0.1 ml calf blood serum (CBS). The mixture was incubated for 0.5 hour at 37° C.

0.1 ml $I^{125}$ labelled *N. gonorrhoeae* antiserum having emanations of approximately 500,000 counts/minute (cpm) was admixed therewith and the mixture incubated for 0.5 hour at 37° C. Thereafter, the mixture was centrifuged for 10 minutes at 5000 rpm and the supernatant decanted off. The precipitate was washed twice with 1 ml CBS for each wash.

Using a conventional gamma ray counter with a scintillator crystal, the following readings were made:

| | |
|---|---|
| Non-specific (background count) | 891 cpm |
| Immobilized antiserum control | 5291 |
| Total count | 599819 |
| Lysate precipitate | 11951 |

The difference in counts/minute between the control and the precipitate is 6660, thereby indicating the presence of 1,2-propanediol dehydrogenase and, consequently, the presence of Neisseria bacteria in the original sample.

EXAMPLE 2

Antiserum was buffered and immobilized on porous glass beads via azo-linkage in like manner to Example 1. Thereafter, 0.1 ml of *N. gonorrhoeae* lysate was mixed with 0.1 ml of immobilized antiserum (about 2.5 mg), 0.1 ml CBS, and 0.6 ml of the buffer solution described in Example 1, and the mixture incubated for 0.5 hour at 37° C. Subsequently, 0.1 ml $I^{125}$ labelled *N. gonorrhoeae* antiserum having emanations of approximately 500,000 cpm was admixed therewith and the resulting mixtures incubated for 0.5 hour at 37° C. This mixture was centrifuged for 10 minutes at 5000 rpm and the supernatant decanted off. The precipitate was washed twice with 1 ml CBS for each wash.

The following table sets out readings which were taken employing a conventional gamma ray counter. Several dilutions of the precipitate are also reported.

| | |
|---|---|
| Non-specific | 667 cpm |
| Immobilized antiserum control | 2954 |
| Total count | 593756 |

| | | Change in cpm |
|---|---|---|
| Undiluted precipitate | 11396 | 8442 |
| 1:2 dilution | 9098 | 6144 |
| 1:4 dilution | 6227 | 3573 |
| 1:8 dilution | 5096 | 2142 |
| 1:16 dilution | 4066 | 1112 |
| 1:32 dilution | 3540 | 585 |

The table points up the sensitivity of the inventive method since detection of Neisseria bacteria is possible at high dilutions of the precipitate.

EXAMPLE 3

Assay of Potentially Cross-Reacting Organisms

Each of the following bacteria samples was grown in five plates. They were washed with 0.1M TRIS, pH 8.0, and subjected to lysis with lysozyme as previously described. Antiserum for *N. gonorrhoeae* was buffered and immobilized on porous glass beads via azo-linkage in accordance with Example 1. Thereafter, 0.1 ml of the individual lysate sample was mixed with 0.1 ml of immobilized antiserum (about 2.5 mg), and 0.8 ml of the buffer solution disclosed in Example 1, and the mixture incubated for 0.5 hour at 37° C. After incubation, the mixture was centrifuged for 10 minutes at 5000 rpm and the supernatant decanted off. The precipitate was then washed twice with the above-described buffer solution using 1 ml of buffer for each wash.

To the washed precipitate were admixed 0.1 ml CBS, 0.8 ml of the above buffer solution, and 0.1 ml $I^{125}$ labelled antiserum for *N. gonorrhoeae* having emanations of approximately 660,000 cpm, and the mixture incubated for 0.5 hour at 37° C. The mixture was then centrifuged for 10 minutes at 5000 rpm and the supernatant decanted off. The precipitate was washed twice with 1 ml CBS for each wash.

The following readings were made utilizing a conventional gamma counter.

| | |
|---|---|
| Non-specific | 1971 cpm |
| Immobilized antiserum control | 2930 |
| Total count | 660000 |

| Sample | cpm recovered undiluted lysate | cpm recovered 1:10 dilution | Test Comment |
|---|---|---|---|
| *Neisseria gonorrhoeae* | 15352 | 4179 | + |
| " | 18383 | 4040 | + |
| " | 10615 | 3586 | + |
| " | 9546 | 3978 | + |
| " | 10505 | 3375 | + |
| " | 10775 | 3975 | + |
| *Enterobacter cloaca** | 4318 | 3831 | — |
| *Klebsiella pneumonae** | 2074 | 2997 | — |
| *Proteus mirabilis** | 3283 | 2896 | — |

*Note very little change on 1:10 dilution of lysate extract.

EXAMPLE 4

Assay of Potentially Cross-Reacting Organisms

Each of the following bacteria samples was grown in a similar manner to Example 3. Likewise, each was washed and lysed in accordance with Example 3. After buffering, antiserum for *N. gonorrhoeae* was immobilized on porous glass beads utilizing the conventional N-hydroxysuccinic ester method. Thereafter, the steps set forth in Example 2 were followed utilizing 0.1 ml $I^{125}$ labelled antiserum for *N. gonorrhoeae* having emanations of approximately 500,000 cpm.

The table below records readings taken with a conventional gamma counter.

| | |
|---|---|
| Non-specific | 609 cpm |
| Immobilized antiserum control | 2857 |
| Total count | 543402 |

| Sample | cpm recovered undiluted lysate | cpm recovered 1:10 dilution | Test Comment |
|---|---|---|---|
| *Neisseria meningitidis* | 9459 | 6062 | + |
| *Neisseria gonorrhoeae* | 14637 | 7882 | + |
| *Branhamella catarrhalis* | 3025 | | — |
| *Staphylococcus aureus* | 2901 | | — |
| *Staphylococcus epidermidis* | 2809 | | — |
| *Escherichia coli* | 3408 | | — |

Examples 3 and 4 illustrate the specificity of the inventive method for Neisseria bacteria when bacterial lysates are prepared as generally described.

Customarily, the operable pH values for lysis will average between about 7–10 with the optimum seemingly in the range of 8–9. Although lysis has been manifested at temperatures approaching 0° C., the reaction rate is significantly increased as the temperature is raised. The rate of reaction appears to reach an optimum at about 50° C., but decreases rather rapidly beyond that value. Consequently, about 60° C. has been considered to represent a reasonable upper temperature. However, the rate of reaction at room temperature (20°–25° C.) has been found to be sufficiently rapid to permit the convenience of utilizing that temperature where desired.

With respect to the antigen-antibody reaction, the operable pH values will again range between about 7–10, but the optimum appears to be between about 7–9. Incubation will take place at about 0° C., but the optimum seems to be about 37° C. with temperatures above about 50° C. being deemed relatively impractical.

It will be recognized that the method disclosed herein can be subject to numerous variations and, hence, the specific exemplary embodiments must be deemed as illustrative only. The scope of the invention is delineated in the appended claims.

I claim:

1. A method for detecting Neisseria bacteria in a sample via an immunoradiometric assay technique comprising the steps:
   (a) preparing a lysate of the sample to be tested;
   (b) bringing radiolabelled antiserum specific to 1,2-propanediol dehydrogenase into contact with the lysate obtained in step (a);
   (c) incubating the mixture resulting from step (b);
   (d) bringing a solid phase antigen or antigen immunoadsorbent into contact with the incubated mixture of step (c);
   (e) incubating the mixture resulting from step (d); and
   (f) monitoring the radioactivity of the supernatant.

2. A method according to claim 1 wherein said sample to be tested is a human body fluid or exudate.

3. A method according to claim 1 wherein said Neisseria bacteria are of the species *N. gonorrhoeae*.

4. A method according to claim 1 wherein said solid phase antigen consists of a substrate inert to the reactants and to which 1,2-propanediol dehydrogenase is immobilized.

5. A method according to claim 4 wherein said substrate is selected from the group of glass, ceramic, and plastic.

6. A method according to claim 4 wherein 1,2-propanediol dehydrogenase is immobilized to said substrate via physical adsorption or chemical coupling.

7. A method according to claim 1 wherein said antigen immunoadsorbent is m-aminobenzylmethyl cellulose.

8. A method according to claim 1 wherein said lysis is carried out at a pH between about 7–10.

9. A method according to claim 1 wherein said lysis is carried out at a temperature between about 0°–60° C.

10. A method according to claim 1 wherein said lysate and antiserum mixture is incubated at a pH of about 7–10.

11. A method according to claim 1 wherein said lysate and antiserum mixture is incubated at a temperature between about 0°–50° C.

12. A method for detecting Neisseria bacteria in a sample via a two-site immunoradiometric assay or sandwich technique comprising the steps:
   (a) preparing an antiserum specific to 1,2-propanediol dehydrogenase;
   (b) immobilizing said antiserum on a substrate;
   (c) preparing a lysate of the sample to be tested;
   (d) applying said lysate onto the immobilized antiserum obtained from step (b);
   (e) incubating the mixture resulting from step (d);
   (f) preparaing a radiolabelled antiserum specific to 1,2-propanediol dehydrogenase;
   (g) contacting said radiolabelled antiserum with the incubated lysate mixture from step (e);
   (h) incubating the mixture resulting from step (g); and
   (i) monitoring the radioactivity of the coated surface of the resulting composite body.

13. A method according to claim 12 wherein said sample to be tested is a human body fluid or exudate.

14. A method according to claim 12 wherein said Neisseria bacteria are of the species *N. gonorrhoeae*.

15. A method according to claim 12 wherein said substrate consists of a material inert to the reactants selected from the group of glass, metal, ceramic, and plastic.

16. A method according to claim 12 wherein 1,2-propanediol dehydrogenase is immobilized on said substrate via physical adsorption or chemical coupling.

17. A method according to claim 12 wherein said lysis is carried out at a pH between about 7–10.

18. A method according to claim 12 wherein said lysis is carried out at a temperature between about 0°–60° C.

19. A method according to claim 12 wherein said lysate and antiserum are incubated together at a pH of about 7–10.

20. A method according to claim 12 wherein said lysate and antiserum are incubated together at a temperature between about 0°–50° C.

* * * * *

UNITED STATES PATENT AND TRADEMARK OFFICE
CERTIFICATE OF CORRECTION

PATENT NO. : 4,188,371
DATED : February 12, 1980
INVENTOR(S) : Howard H. Weetall It is certified that error appears in the above-identified patent and that said Letters Patent are hereby corrected as shown below:

Column 2, line 4, change "on" to -- an --.

Column 4, line 57, change "0.3M" to -- 0.03M --.

Column 6, line 28, change "0.3M" to -- 0.03M --.

*Signed and Sealed this*

*Tenth Day of June 1980*

[SEAL]

*Attest:*

*Attesting Officer*

SIDNEY A. DIAMOND

*Commissioner of Patents and Trademarks*